United States Patent
Kirakosyan

(10) Patent No.: US 9,427,394 B2
(45) Date of Patent: Aug. 30, 2016

(54) HAIR LOSS PREVENTION AND RESTORATION SOLUTION

(71) Applicant: Ruzanna Kirakosyan, Sunland, CA (US)

(72) Inventor: Ruzanna Kirakosyan, Sunland, CA (US)

( * ) Notice: Subject to any disclaimer, the term of this patent is extended or adjusted under 35 U.S.C. 154(b) by 0 days.

(21) Appl. No.: 14/320,176

(22) Filed: Jun. 30, 2014

(65) Prior Publication Data

US 2015/0374613 A1    Dec. 31, 2015

(51) Int. Cl.
| | |
|---|---|
| *A61K 36/00* | (2006.01) |
| *A61K 8/92* | (2006.01) |
| *A61K 8/97* | (2006.01) |
| *A61K 8/65* | (2006.01) |
| *A61K 8/34* | (2006.01) |
| *A61K 8/37* | (2006.01) |
| *A61K 8/36* | (2006.01) |
| *A61K 8/39* | (2006.01) |
| *A61Q 7/00* | (2006.01) |

(52) U.S. Cl.
CPC ............... *A61K 8/922* (2013.01); *A61K 8/345* (2013.01); *A61K 8/36* (2013.01); *A61K 8/37* (2013.01); *A61K 8/39* (2013.01); *A61K 8/65* (2013.01); *A61K 8/97* (2013.01); *A61Q 7/00* (2013.01); *A61K 2800/5922* (2013.01)

(58) Field of Classification Search
None
See application file for complete search history.

*Primary Examiner* — Qiuwen Mi
(74) *Attorney, Agent, or Firm* — Adli Law Group P.C.

(57) ABSTRACT

The embodied invention generally pertains to compositions, and the methods of making and using said compositions for promoting hair growth, slowing hair loss, and for preventing or minimizing hair loss that are effective and able to treat multiple aspects of the problem in one product and additionally is comprised of natural oils and minerals which greatly reduce the toxicities and side effect issues associated with present products. The compositions or formulations of the present invention relate to a hair loss solution that solves the problems associated with the loss, and damage of hair by working from the root to the surface of the scalp and to the hair shaft by treating a plurality of the causes and/or triggers associated with hair loss, or the prevention of hair re-growth.

4 Claims, 1 Drawing Sheet

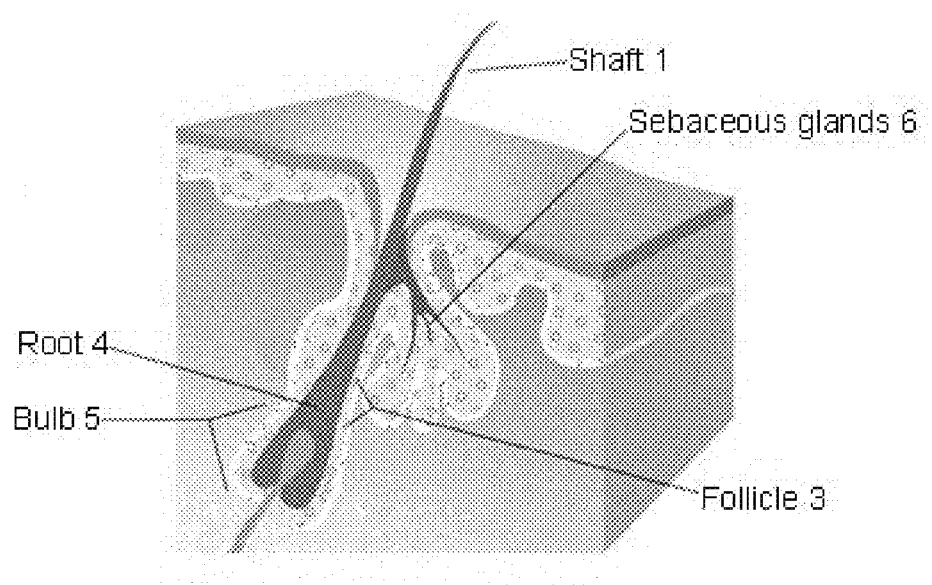

HAIR LOSS PREVENTION AND RESTORATION SOLUTION

BACKGROUND OF THE INVENTION

There are many products on the market claiming to provide a solution to hair loss, however the products generally only treat one or two aspects of the problem or mask the problem altogether. There are multiple reasons for hair loss and damaged hair.

Hair loss or alopecia may be caused by a variety of factors including heredity, hormonal deficiencies or imbalances, diet, stress, illnesses, chemotherapy or aging. The desire to maintain or regain head hair has led to continuing efforts throughout history to discover compositions and methods for stimulating hair growth and for preventing or minimizing hair loss.

For many years, the pharmaceutical industry, the nutraceutical industry, and the cosmetic industry have been researching and developing compositions in attempts to cure or prevent hair loss or promote hair growth.

There are surgical and non-surgical solutions to address the problem of hair loss. Non-surgical options for treating hair loss include a variety of pharmaceutical and nutraceutical topical and/or oral treatments that promote hair regrowth and/or prevent further hair loss. For example, topical minoxidil, commonly known as ROGAINE, causes hair growth when applied to the scalp and slows the rate of hair loss in some individuals by stimulating hair follicles. Finasteride, commonly known as PROPECIA is a drug that is taken orally to treat androgenic alopecia by blocking the formation of DHT. The problem with treating hair loss with pharmaceutical drugs is the potential side effects of such drugs. Minoxidil may cause low blood pressure, increase in heart rate, weight gain due to water retention, and the scalp may become inflamed. Finasteride may cause genital deformities in male infants, impotence, decreased libido, hives or rash, and swelling.

Thus, in spite of the advancements in the prior art, there is a need in the art for compositions for promoting hair growth, slowing hair loss, and for preventing or minimizing hair loss that are effective and able to treat multiple aspects of the problem in one product and additionally is comprised of natural oils and minerals which greatly reduce the toxicities and side effect issues of present products, and for methods of making and using such compositions.

SUMMARY OF THE INVENTION

The embodiments of the present invention generally relate to hair loss prevention and restoration products and more specifically to specific formulations used to improve user outcomes in regards to hair loss and prevention, by treating a plurality of the causes associated with hair loss in a single formulation.

Additional embodiments include compositions for promoting hair growth, slowing hair loss, and for preventing or minimizing hair loss that are effective and able to treat multiple aspects of the hair loss problem in one product and additionally is comprised of natural oils and minerals which greatly reduce the toxicities and side effect issues of present products, and for methods of making and using such compositions.

Embodiments of the present invention comprise of a formulation of different oils and plant extracts that when formulated together, are able to reconstruct and rejuvenate the hair follicle, and scalp in order to restore hair growth and prevent further hair loss.

An embodiment of the present invention comprises of a formulation for use in the treatment of hair loss comprising: Rose water, Eucalyptus oil, Castor oil, Thyme oil, Rosemary Oil, German Chamomile Oil, Carrot Oil, Cederwood oil, Grape seed oil, Arnica oil, and Pseudocollagen. Further embodiments may also include at least one of the oils selected from coconut oil, sweet almond oil, olive oil, lavender oil, jojoba oil, aloe vera oil, tea tree oil or coconut oil. Still further embodiments may also include at least one of the ingredients selected from Vegetable glycerin, Shea Butter, Sage oil, Polyglyceryl Oleate, or PEG-7-Glyceryl Cocoate.

An additional embodiment includes a formulation including a total volume percent range for each ingredient including; 25% to 30% Rose water, 5% to 10% Eucalyptus oil, 5% to 8% Castor oil, 5% to 8% Thyme oil, 4% to 6% Rosemary Oil, 3% to 5% German Chamomile Oil, 3% to 5% Carrot Oil, 2% to 4% Coconut Oil, 2% to 4% Sweet Almond Oil, 1% to 3% Cederwood Oil, 1% to 3% Olive Oil, 1% to 3% Grape seed Oil, 1% to 3% Lavender Oil, 0.5% to 2.5% Arnica Oil, 0.5% to 2.5% Jojoba Oil, 0.5% to 2.0% Aloe Vera Oil, 0.5% to 2.0% Tea Tree Oil, 0.5% to 2.0% Pseudocollagen, 0.5% to 2.0% Vegetable glycerin, 0.5% to 2.0% Shea Butter, 0.1% to 0.6% Sage Oil, 8% to 12% Polyglyceryl Oleate, and 2% to 4% PEG-7-Glyceryl Cocoate.

A further additional embodiment includes a formulation with a total volume percentage for each ingredient including; 28.8% Rose water, 7.4% Eucalyptus Oil, 6.4% Castor Oil, 6.4% Thyme Oil, 5.3% Rosemary Oil, 4.3% German Chamomile Oil, 4.3% Carrot Oil, 3.2% Coconut Oil, 3.2% Sweet Almond Oil, 2.1% Cederwood Oil, 2.1% Olive Oil, 2.1% Grape seed Oil, 2.1% Lavender Oil, 1.6% Arnica Oil, 1.6% Jojoba Oil, 1.1% Aloe Vera Oil, 1.1% Tea Tree Oil, 1.1% Pseudocollagen, 1.1% Vegetable glycerin, 1.1% Shea Butter, 0.3% Sage Oil, 10.6% Polyglyceryl Oleate, and 2.7% PEG-7-Glyceryl Cocoate.

Additional methods include methods of using the embodied formulations as described above to help prevent treat and restore hair regrowth and general scalp and hair health.

Yet further embodiments include methods for formulating the formulations as described above.

BRIEF DESCRIPTION OF THE DRAWINGS

FIG. 1 demonstrates an illustration of a hair shaft in relation to the scalp.

DETAILED DESCRIPTION OF THE PREFERRED EMBODIMENT(S)

FIG. 1 demonstrates a reference illustration of the anatomical components associated with hair and the scalp. The embodiments of the present invention relate to a hair loss solution that solves the problems associated with the loss, and damage of hair by working from the root 4 to the surface of the scalp 2 and to the hair shaft 1. Although there are many products that claim to work from the root 4 to the surface of the scalp 2 and the hair shaft 1, these products generally only treat one or two of the reasons or triggers that cause the underlying event or even worse they may mask these reasons or triggers leading to hair loss altogether.

As used herein, the term "hair loss" refers to loss of hair from the scalp or thinning of hair. The term "prevention of hair loss" refers to prevention and inhibition of the hair loss.

And, the term "enhancement of hair growth" refers to enhancement of growth of new hair or healthy growth of existing hair.

Hair growth is affected by various factors including environmental factors such as temperature or sunlight, nutritional status of individuals and presence/absence of diseases, hormones, childbirth, exposure to radiation or various drugs, and so forth. The main causes of hair loss can be largely divided into internal physiological factors and external environmental factors. The internal physiological factors include, for example, increased activity of 5-alpha reductase which increases sebum secretion (from the sebaceous glands 6) by converting testosterone, an androgen, into dihydrotestosterone (DHT). The external environmental factors include, for example, malnutrition of the hair bulb 5 owing to insufficient blood circulation caused by constriction of blood vessels, dryness of the scalp 2, or the like. Accordingly, in order to prevent hair loss and enhance hair growth, it is necessary to nourish the hair bulb 5 by dilating blood vessels, supply substances that serve the same function as the constituents of hair directly to the hair bulb 5, remove excess sebum around the hair bulb 5 using a cleanser or an anti-sebum agent, or prevent dryness of the scalp using a moisturizer.

Because there are multiple triggers and reasons for hair loss and damaged hair as described above, the embodiments of the present invention are formulated to treat and minimize the problems that a person would have with their scalp 2 and hair 1 by addressing a broad range of hair loss triggers and reasons in a single formulation. The embodied product works with the scalp 2 and hair 1 to balance the pH to normal. Furthermore, the embodied formulation stabilizes the past, present and the future of the hair. In its first stage, an embodied formulation detoxifies the hair follicle 3 from all impurities from past products or internal impurities and stops the hair loss. In its second stage, the embodied formulations create better conditions for the hair 1 to grow by nourishing and strengthening the hair follicle 3. At the third stage, the formulation exhilarates hair re-growth. And at its fourth stage the formulation nourishes the hair from the root 4 to the tip of the hair 1. By nourishing the hair follicle 3 the hair shaft 1 is additionally nourished. The end result is beautiful and healthy looking hair that is healthy from the inside out. Users' notice the difference in the hair and that the hair has more body and shine. The combination of ingredients in the embodied formulations work together to produce great results for users experiencing hair loss and/or thinning and generally damaged hair.

The embodied formulations are generally comprised of all-natural products. The embodied formulations comprise of different oils and plant extracts and are formulated to reconstruct and rejuvenate the hair follicle in order to restore the hair. The embodied formulations help to stop the hair loss and rejuvenate the hair by restoring and nourishing the hair follicle.

Additionally, the embodied formulations may help with hair loss caused by illnesses, stress or environmental and chemical causes. The embodied formulations work by penetrating into the hair follicle, and detoxifying, nourishing and restoring the hair follicle to a more healthy form. This detoxification, nourishment and restoration of the hair follicle may be evident to a user after a single use, wherein the hair appears healthier, shinier, and more full of body and movement. Over time the user will notice that the hair becomes fuller and thicker. Unlike many products in the prior art the embodied formulations treat the root of the problem and does not mask the shortcomings by treating only the symptoms of unhealthy hair causing hair loss.

For best results using the embodied formulations the user first washes their hair and scalp thoroughly. The hair is towel dried and the formulation is applied to the hair and scalp by massaging the formulation on to the scalp. The formulation is then left on the scalp and in the hair for 20-30 minutes before it is rinsed out. In an optimized process for restoring hair and preventing hair loss the embodied formulations are applied as described above about 4 times a week for the first month and then tapered to 2 times a week thereafter. The more concentrated efforts at the beginning of the process help jumpstart the recovery of the hair follicle.

The studies with the formulations embodied showed a noticeable decrease in hair loss after 3-4 applications of the embodied formulations. Additionally, the hair was noticeably starting to re-grow after 1-3 months of use.

Studies were conducted on people with different issues associated with the hair and scalp. Some of the study participants had massive hair loss due to stress and/or medication, others from thyroid or other health related issues.

The people who had hair loss caused by stress, environment and medication had faster results. However, people with hair loss caused by thyroid and other health issues still showed positive results but more treatments were generally necessary before signs of improvement were observable.

Hair loss caused by secondary health issues showed faster results in improving the conditions of the scalp and hair. However, hair loss caused by primary health conditions were observed to take longer depending on the nature of the illness. In most people with secondary health issues, hair loss was noticeably decreased in 2-4 weeks. However, a person with primary health issues took about 6 to 12 weeks to notice the prevention of hair loss and the change in the texture of the hair, the time range was highly dependent what type of illness was associated with the primary health issue.

Any illness can and does effect the health of the rest of the body and its ability to properly nourish the skin and the hair internally. The embodied formulations maintain the nourishment of the skin and hair externally. The embodied formulations of the present invention help fill in the nutritional gaps that may be caused by the illness or malnourishment of the scalp and hair. Thereby, making the hair follicle strong enough to continuously maintain a healthy structure.

A list including the detailed information of the contemplated ingredients in the embodied formulations include:

Rose water. Rose water is known to have anti-inflammatory properties and to soothe irritated skin, it is also a great source of antioxidants which help to strengthen skin cells and regenerate skin tissue. Additionally, Rose water is known to stimulate the circulation of tiny blood vessels underneath the skin. Furthermore, Rose water assists in maintaining the skins pH balance, calms dermatitis and eczema. Rose water is known to hydrate and revitalize the skin while healing scars, cuts, and wounds that may be caused by various natural factors such as accidents, as well as from chemical damage to the scalp. Additionally, Rose water helps to hydrate and condition the hair shaft and helps make the hair shaft strong and flexible in order to help resist hair breakage.

Castor oil. Castor oil comprises vital components including nutrients, proteins, minerals and vitamin E which are all required for healthy hair. Castor oil is also rich in anti-bacterial and anti-fungal properties and has many fatty acids including ricindeic acid. Ricindeic acid helps to protect the hair and stimulates circulation of nutrient rich blood to the scalp. Furthermore, the full range of amino acids and omega-6 fatty acids found in castor oil help prevent split ends and hair breakage. Castor oil has the ability to penetrate deep in to the scalp and to smooth out rough hair and cuticles.

Thyme oil. Thyme oil is beneficial for scalp health and hair re-growth, the oil is powerfully concentrated and contains thymol, which is known to have antiseptic properties. Thyme oil provides benefit for cleansing and renewing the hair follicle. Thyme oil further contains pro-vitamin A, vitamin C and Keratin which are known to improve hair health.

Rosemary oil. Rosemary oil is one of the premier hair growth enhancing essential oils, which stimulate healthy hair growth. It is successfully used in Alopecia areata (hair-loss) treatment. Rosemary oils slow down premature hair loss and graying of hair. Rosemary oil is also beneficial for treating flaky scalps. Rosemary has the ability to strengthen the scalp and is beneficial in efforts to eliminate eczema, dermatitis and oily scalp.

German Chamomile Oil. German Chamomile oil is known to help calm eczema, rashes, wounds, dermatitis, dry and itchy skin. The oil is known to have anti-inflammatory and anti-infectious properties and also helps to calm allergic reactions to chemicals. The oil helps to regenerate skin tissue and may revitalize hair by straightening its root.

Coconut oil. Coconut oil is comprised of natural antioxidants and nutrients which when applied to hair help improve its softness and luster. The oil is rich in vitamin E, vitamin K and iron and effectively eliminates dandruff while boosting hair growth. Coconut oil effectively improves scalp circulation and boosts nutrient and oxygen delivery to hair. The fatty acids found within coconut oil bind to the protein in hair and protect both the roots and shaft of the hair from breakage. Specifically, Lauric acid, found in coconut oil improves hair health. Coconut oil serves two main functions when added to the embodied hair healing and protection embodiments. First, coconut oils hydrophobic properties allow it to inhibit the penetration of water from the surrounding air and environment. And second, coconut oil is able to bind to the natural protein structure of the hair, which helps hair retain it natural moisture content and reinforces the hair fiber thus, making it stronger.

Sweet almond oil. Sweet almond oil is a rich source of vitamins A, B, and E. The oil assists with the removal of dead skin cells and impurities as well as reduces inflammation, redness and itching of skin. Sweet almond oil is a good emollient and has properties that make it very useful for treating skin problems such as psoriasis and eczema. Sweet almond oil stimulates hair growth, strengthens hair reducing hair breakage and adds shine, smoother ends and less frizz.

Lavender oil. Not only is lavender good for the mind, but it is also beneficial for a healthy scalp and hair growth. Because lavender oil is a natural anti-inflammatory, it is helpful for maintaining a healthy scalp and can be used to treat dandruff and psoriasis of the scalp. By keeping these scalp conditions at bay, and enhancing the blood circulation of the scalp, the scalp is rejuvenated and shows signs of improved health. Additionally, Lavender oil enhances blood circulation, to further improve the health of the scalp.

Olive oil. One of the more surprising benefits of olive oil is that it can prevent and even cure hair loss. When people lose hair, it is due to a hormone responsible for the shrinkage of the hair follicle shaft. However, the production of that hormone, called DHT (dihydrotestosterone), is hampered when olive oil is applied to the scalp. The overall health of the scalp also benefits from olive oil and a healthy scalp equates to healthy hair. Additionally, the natural conditioner properties of olive oil add moisture to the scalp, an area that people tend to neglect. Besides healing a dry scalp; olive oil makes hair soft and shiny and has antibacterial and antifungal properties that fight off common scalp and hair problems. Furthermore, the application of Olive oil to the scalp can prevent or hamper dandrugg or even head lice.

Grape seed oil. Grape seed oil helps hair to grow faster, and the essential oil contains almost all the important nutrients for hair to grow healthily. It has vitamin E, linoleic acid, proteins and minerals that nourish the hair and scalp almost instantly after the oil is topically applied. In general, hair grows faster and stronger when it is provided with a nourishing supply of vitamin E and other important nutrients. Additionally, Grape seed oil has several important health benefits in that it is a good source of essential fatty acids and vitamin E, also the polyphenols and flavonoids found in the oil contain strong antioxidant compounds. Furthermore, the flavonoid 'oligomeric procyanidin', found in grape seed oil is an incredibly strong antioxidant, about 50 times stronger than antioxidants such as vitamin C and E which allows grape seed oil containing this flavonoid to be a very strong free radical scavenger and provide protection against cellular and tissue damage caused by free radicals. Additionally, Grape seed oil can help strengthen and repair damaged or broken capillaries and blood vessels.

Carrot oil. Carrot oil is an effective hair and a skincare emulsion because it is rich in carotene, antioxidants and amino acids. Carrot oil is great for skin renewal as well as hair growth. It also revitalizes and tones the skin, helping in cases of dermatitis, eczema and rashes. Since carrot seed oil contains carotene and vitamin A, it is also very good for healthy skin and hair.

Arnica oil. Arnica oil helps speed the healing process of hair and tissues by moving waste-bound fluids out and moving cleansing fluids and platelets into an affected area. Arnica oil is considered as one of the best ethereal oils to prevent hair loss and it is a trusted herbal cure for alopecia neurotic. Arnica oil based preparations are also well known in homeopathy as a cure for various hair related problems such as diffuse alopecia, graying hair and dandruff. Additionally, Arnica oil is a strong anti-inflammatory agent with antioxidant properties that enrich the scalp and protect hair from damage caused by harsh elements and environmental pollution.

Tea Tree Oil. Tea Tree oil helps to remove dead skin cells and is a powerful scalp purifier. The oil may be used to treat scalp conditions such as psoriasis and dandruff and promotes hair growth by improving blood circulation all over the scalp. Tea tree oil encourages seating which, in turn, leads to detoxification of the skin as pollutants and a lot of infectious agents are flushed out of the body.

Pseudocollagen. Pseudocollagen (Yeast-derived collagen equivalent): This yeast-derived, dermal-matrix material is a true moisturizing glycoprotein taken from living cells. It is extracted from yeast by a controlled process which preserves its high molecular weight and native structure, making it the perfect addition to skin and hair products. Pseudocollagen can be used in a wide variety of hair-care formulas, providing body and shine, and leaving permed hair with a softer, less raspy look.

Eucalyptus Oil. Eucalyptus oil increases the elasticity of hair making it stronger and more resistant to hair breakage and split ends. The oil has antiseptic and antifungal properties, and can keep the scalp healthy by preventing microbial growth. Which, in turn can promote healthy growth of hair. This oil is effective at getting rid of dandruff, which is a common scalp problem that can cause hair loss. Dandruff can also inhibit the growth of hair. Eucalyptus oil can provide relief in other scalp problems, such as mild forms of psoriasis, scalp pimples, and dry scalp. Additionally, the oil can moisturize and soothe dry skin and improve blood flow to the scalp, which can help eliminate the build up of oil and bacteria in the hair follicles. Because proper blood circulation ensures the supply of adequate nutrients to the hair follicles, which stimulates hair growth, by improving scalp circulation this oil can revitalize dull hair and improve hair texture. Eucalyptus oil also increases the production of ceramide, a type of lipid molecule that naturally occurs in hair strands. Ceramides help keep the hair cuticle intact, and prevent the loss of natural moisture and protein from hair strands. This in turn increases the strength, shine, and elasticity of hair.

Cedarwood oil. Cedarwood essential oil has powerful antiseptic, anti-seborrheic, astringent and fungicidal properties which makes it an effective cure and prevention agent for fungal infections of the scalp and irritating dandruff conditions. The astringent properties of the oil help deep cleanse the scalp and hair shaft to allow the roots and follicles to breathe, whereas the anti-seborrheic properties correct imbalanced functioning of the sebaceous glands by arresting excess sebum production.

Avocado oil. Avocado oil is full of healthy hair vitamins that promote and maintain silky locks of hair. The oil also contains amino acids that help bind split ends, nourish hair follicles and promote faster hair growth. The various nutrients in avocado oil protect hair from environmental pollution. Additionally the oil can strengthen hair strands, add a dash of shine and make hair super soft.

Jojoba oil. Jojoba oil has antibacterial and fungicidal properties, that can be used for keeping the scalp healthy. The oil aids in reducing hair loss, caused by factors like scalp dermatitis, psoriasis, and eczema. Jojoba oil is an excellent hair conditioner, which can be used to get rid of dry, frizzy, and unmanageable hair. Additionally, the oil helps seal the moisture in the hair shaft, and adds a natural glow and luster to hair by minimizing the damage caused by harsh chemicals and pollutants.

Shea Butter. The main components of shea butter include oleic acid, stearic acid, linoleic acid and others. The butter is absorbed quickly into the skin as it melts at body temperature. Shea butter is known for its healing properties, which can be attributed to the presence of several fatty acids and plant sterols such as oleic, palmitic, stearic and linolenic acids. These oil-soluble components do not undergo saponification or convert into soap upon coming into contact with alkali. Additionally, Shea butter is more non-saponifiable than other nut oils and fats, thus imparting it a great healing potential for the skin. The butter contains plant antioxidants such as vitamins A and E, as well as catechins. The vitamins A and E protect the cells from free radicals and environmental damage. Furthermore Shea butter has cinnamic acid esters in the shea fat which help in preventing skin damage from ultraviolet radiation. Several derivatives of cinnamic acid are found in shea butter which exhibit anti-inflammatory properties. Being rich in precious constituents such as unsaturated fats with a large proportion of non-saponifiable components, essential fatty acids, vitamins E and D, phytosterols, provitamin A and allantoin, shea butter is considered a super food for the skin.

Aloe Vera oil. Aloe Vera oil provides a great benefit for hair loss prevention as well as removing dandruff and treating seborrhea. When dandruff occurs there is usually an accompanying hair loss problem. In fact, in order to properly treat hair loss one needs to first handle the dandruff problem. The natural pH level of hair and scalp is between 4 and 4.5, while aloe vera's pH level is 4.5 to 5.5. Therefore, the plant can be used to restore hair and scalp to its natural condition without using additional chemical substances. A proper pH level of the hair and scalp helps the hair maintain its ability to retain moisture.

Sage oil. Sage oil is among the best scalp purifiers. A strong infusion of Sage essential oil used as a rinse is believed to darken gray hair and is among the most trusted herbal loss solutions. Additionally, Sage oil is loaded with antioxidant, antiseptic and antifungal properties.

Polyglyceryl Oleate. Polyglyceryl Oleate is a distilled triyglycerol ester based on vegetable oleic acid, that is PEG-free. It is a yellow to amber liquid in color and has a bland odor. Polyglyceryl Oleate disperses in water and has a hydrophilic-lipophilic balance (HLB) of 5 (gives water-in-oil emulsions). The INCI Name is Polyglyceryl-4oleate. The general chemical properties of Polyglyceryl Oleate make it an excellent emulsifier (which freely enables water & oil to mix).

PEG-7 Glyceryl Cocoate. Description: Non-ionic, ethoxylated polyethylene glycol ester made from glycerin & coconut oil. It is a clear oily liquid, with a characteristic odor. The compound is soluble in water & alcohols, but insoluble in oils. The HLB value is 11 (gives oil-in-water emulsions). The CAS# is 68201-46-7 and the INCI Name is: Polyoxyethylene (PEG-7) glyceryl monococoate. The compound properties are that it is a Multifunctional agent with excellent emulsifying, emollient, refatting & thickening properties, and is useful as a surfactant & foam booster, and has good conditioning effects for soft & smooth skin.

By formulated combinations of the above ingredients listed above in a single formulation the end result is a powerhouse formulation with the ability to stop and prevent hair loss, fast and effectively. The combination of the selected ingredients work together to straighten, clarify, neutralize and heal the scalp. The embodied formulations are a medicine for hair and scalp. They heal from the root to the ends of the hair. The embodied formulations are able to penetrate deep in to the layers of skin. And have the ability to clarify the hair follicle from impurities and unclog the follicle. By unclogging the hair follicle the formulation allows the hair to grow and expand without any restrictions. Thus creating the ideal environment for re-growth of healthy hair. Embodied formulations are also able to rebuild the damaged tissue over a short amount of time making it ideal for those with chemically damaged scalps to regenerate the ability to produce healthy hair. Additionally, the embodied formulations assist those with skin issues, calms dermatitis, eczema and other skin related issues. Each ingredient is unique in their own way, however when combined together at a proper ratio there is a synergy of components that allows the formulation to have a noticeable effect after the first use.

Details of the present invention will now be discussed by reference to the following non-limiting examples.

| Ingredients | Oz | Total % | Range |
|---|---|---|---|
| Rose water | 54 | 28.8% | 25-30% |
| Eucalyptus oil | 14 | 7.5% | 5-10% |
| Castor oil | 12 | 6.4% | 5-8% |
| Thyme oil | 12 | 6.4% | 5-8% |
| Rosemary Oil | 10 | 5.3% | 4-6% |
| German Chamomile oil | 08 | 4.3% | 3-5% |

-continued

| Ingredients | Oz | Total % | Range |
|---|---|---|---|
| Carrot Oil | 08 | 4.3% | 3-5% |
| Coconut oil | 06 | 3.2% | 2-4% |
| Sweet almond oil | 06 | 3.2% | 2-4% |
| Cederwood oil | 04 | 2.1% | 1-3% |
| Olive oil | 04 | 2.1% | 1-3% |
| Grape seed oil | 04 | 2.1% | 1-31-3% |
| Lavender oil | 04 | 2.1% | .5-2.5% |
| Arnica oil | 03 | 1.6% | .5-2.5% |
| Jojoba oil | 03 | 1.6% | .5-2.0% |
| Aloe Vera oil | 02 | 1.1% | .5-2.0% |
| Tea tree oil | 02 | 1.1% | .5-2.0% |
| Pseudocollogen | 02 | 1.1% | .5-2.0% |
| Vegetable glycerin | 02 | 1.1% | .5-2.0% |
| Shea Butter | 02 | 1.1% | .5-2.0% |
| Sage oil | 0.5 | 0.3% | 0.1-0.6% |
| Polyglyceryl Oleate | 20 | 10.7% | 8-12% |
| PEG-7-Glyceryl Cocoate | 5 | 2.7% | 2-4% |
| Total oz | 187.5 | | |

EXAMPLE FORMULATION 1

Methods of Formulating the product. The methods of formulating utilize two containers, a first container has the oils and other ingredients and the second container has the rose water and the emulsifiers. The exemplary formulation batch shown includes a final batch amount of about 187.5 ounces.

Step 1

In a first container the following ingredients are mixed together in the following amounts: 14 oz of Eucalyptus oil, 12 oz of Castor oil, 12 oz of Thyme oil, 10 oz of Rosemary oil, 8 oz of German Chamomile oil, 8 oz if Carrot oil, 6 oz of Coconut oil (melted in a pot before adding), 6 oz of Sweet almond oil, 4 oz of Cederwood oil, 4 oz of Olive oil, 4 oz of Grape seed oil, 4 oz of Lavender oil, 3 oz of Arnica oil, 3 oz of Jojoba oil, 2 oz of Aloe Vera oil, 2 oz of Tea tree oil, 2 oz of Pseudocollagen, 2 oz of Vegetable glycerin, 2 oz of Shea Butter (Melted in a pot before adding), 0.5 oz of Sage oil.

Step 2

In a second container the following ingredients are mixed together in the following amounts: 54 oz of Rose water, 20 oz of Polyglyceryl Oleate, and 5 oz of PEG-7-Glyceryl Cocoate.

Step 3

After step 1 and 2 are complete the ingredients from the first container are slowly stirred into the second container ingredients and mixed. After mixing the ingredients together the formulation comprises a creamy serum that is ready to be used.

In other exemplary embodiments, the formulation may be changed and various other ingredients may be added to change some of the characteristics of the formulation to create gels, mousses, shampoos, conditioners, rinses and the like. The application of these products may vary depending upon whether the user is trying to prevent the loss of hair or trying to grow hair.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. In other exemplary embodiments, the formulation may be changed and various other ingredients may be added to change some of the characteristics of the formulation to create gels, mousses, shampoos, conditioners, rinses and the like. The application of these products may vary depending upon whether the user is trying to prevent the loss of hair or trying to grow hair. Additionally, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A formulation for use in the treatment of hair loss comprising:
   20% to 30% Rose water, 5% to 10% Eucalyptus oil, 5% to 8% Castor oil, 5% to 8% Thyme oil, 4% to 6% Rosemary Oil, 3% to 5% German Chamomile Oil, 3% to 5% Carrot Oil, 1% to 3% Cedarwood oil, 1% to 3% Grape seed oil, 0.5% to 2.5% Arnica oil, 0.5% to 2.0% Pseudocollagen, 0.5% to 2.0% Vegetable glycerin, 0.5% to 2.0% Shea Butter, 0.1% to 0.6% Sage oil, 8% to 12% Polyglyceryl Oleate, and 2% to 4% PEG-7-Glyceryl Cocoate.

2. A formulation for use in the treatment of hair loss comprising:
   25% to 30% Rose water,
   5% to 10% Eucalyptus oil,
   5% to 8% Castor oil,
   5% to 8% Thyme oil,
   4% to 6% Rosemary oil,
   3% to 5% German Chamomile oil,
   3% to 5% Carrot oil,
   2% to 4% Coconut oil,
   2% to 4% Sweet Almond oil,
   1% to 3% Cedarwood oil,
   1% to 3% Olive oil,
   1% to 3% Grape seed oil,
   1% to 3% Lavender oil,
   0.5% to 2.5% Arnica oil,
   0.5% to 2.5% Jojoba oil,
   0.5% to 2.0% Aloe Vera oil,
   0.5% to 2.0% Tea Tree oil,
   0.5% to 2.0% Pseudocollagen,
   0.5% to 2.0% Vegetable glycerin,
   0.5% to 2.0% Shea butter,
   0.1% to 0.6% Sage oil,
   8% to 12% Polyglyceryl Oleate, and
   2% to 4% PEG-7-Glyceryl Cocoate.

3. The formulation claim 2 wherein a total volume percentage for each ingredient is:
   28.8% Rose water,
   7.4% Eucalyptus oil,
   6.4% Castor oil,
   6.4% Thyme oil,
   5.3% Rosemary oil, 4.3% German Chamomile oil,
4.3% Carrot oil,
3.2% Coconut oil,
3.2% Sweet Almond oil,
2.1% Cedarwood oil,
2.1% Olive oil,
2.1% Grape seed oil,
2.1% Lavender oil,
1.6% Arnica oil,
1.6% Jojoba oil,
1.1% Aloe Vera oil,
1.1% Tea Tree oil,
1.1% Pseudocollagen,
1.1% Vegetable glycerin,
1.1% Shea butter,
0.3% Sage oil,
10.6% Polyglyceryl Oleate, and
2.7% PEG-7-Glyceryl Cocoate.

4. A method for promoting hair health comprising administering an effective amount of the formulation of claim 3.

* * * * *